(12) United States Patent
Bokka Srinivasa Rao et al.

(10) Patent No.: US 10,578,606 B2
(45) Date of Patent: Mar. 3, 2020

(54) DEPTH FILTRATION DEVICE FOR SEPARATING SPECIMEN PHASES

(71) Applicant: Becton, Dickinson and Company, Franklin Lakes, NJ (US)

(72) Inventors: Kishore K. Bokka Srinivasa Rao, Ridgewood, NJ (US); Daniel J. Marchiarullo, Morris Plains, NJ (US); Milan Ivosevic, Kinnelon, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 0 days.

(21) Appl. No.: 15/252,804

(22) Filed: Aug. 31, 2016

(65) Prior Publication Data

US 2017/0059550 A1 Mar. 2, 2017

Related U.S. Application Data

(60) Provisional application No. 62/212,797, filed on Sep. 1, 2015.

(51) Int. Cl.
*G01N 33/49* (2006.01)
*B01D 15/10* (2006.01)
(Continued)

(52) U.S. Cl.
CPC ..... *G01N 33/491* (2013.01); *A61B 5/150022* (2013.01); *A61B 5/150343* (2013.01); *A61B 5/150358* (2013.01); *B01D 15/10* (2013.01); *B01L 3/502* (2013.01); *B01L 3/5023* (2013.01); *B01L 2200/026* (2013.01); *B01L 2200/0652* (2013.01); *B01L 2300/042* (2013.01);
(Continued)

(58) Field of Classification Search
CPC ........ G01N 33/491; A61B 5/14; B01D 15/10; B01L 3/502; B01L 3/5023
USPC ................................ 422/513, 527, 534–535
See application file for complete search history.

(56) References Cited

U.S. PATENT DOCUMENTS 2,895,773 A 7/1959 McConnaughey
3,819,913 A 6/1974 Carter et al.
(Continued)

FOREIGN PATENT DOCUMENTS

DE 2514412 A1 10/1976
EP 0545500 A1 6/1993
(Continued)

OTHER PUBLICATIONS

Bruil, A. (1991). "Asymmetric membrane filters for the removal of leukocytes from blood." J. Biomed. Mater. Res. 25:1459-1480. (Year: 1991).*

(Continued)

*Primary Examiner* — Brian R Gordon
(74) *Attorney, Agent, or Firm* — The Webb Law Firm

(57) ABSTRACT

The present disclosure provides a biological fluid collection device, such as a blood collection device, that is adapted to receive a multi-component blood sample having a cellular portion and a plasma portion and quickly, efficiently and cost-effectively separate the plasma portion from the sample. A pressure gradient can be applied across a separation member to facilitate movement of the plasma portion ahead of the cellular portion. The present disclosure allows for both passive and active plasma separation and dispensing.

16 Claims, 13 Drawing Sheets

(51) Int. Cl.
 *B01L 3/00* (2006.01)
 *A61B 5/15* (2006.01)
(52) U.S. Cl.
 CPC . *B01L 2300/048* (2013.01); *B01L 2300/0609* (2013.01); *B01L 2300/0681* (2013.01); *B01L 2300/087* (2013.01); *B01L 2300/0838* (2013.01); *B01L 2300/123* (2013.01); *B01L 2300/14* (2013.01); *B01L 2300/161* (2013.01); *B01L 2400/0406* (2013.01); *B01L 2400/049* (2013.01); *B01L 2400/0481* (2013.01)

(56) References Cited

U.S. PATENT DOCUMENTS

| | | |
|---|---|---|
| 3,916,205 A | 10/1975 | Kleinerman |
| 3,939,833 A | 2/1976 | Hansson et al. |
| 3,963,350 A | 6/1976 | Watanabe et al. |
| 4,088,448 A | 5/1978 | Lilja et al. |
| 4,125,828 A | 11/1978 | Resnick et al. |
| 4,133,304 A * | 1/1979 | Bailey ............ A61B 5/15003 600/577 |
| 4,133,873 A | 1/1979 | Noller |
| 4,266,557 A | 5/1981 | Merry |
| 4,337,222 A | 6/1982 | Kitajima et al. |
| 4,343,705 A | 8/1982 | Legg |
| 4,501,496 A | 2/1985 | Griffin |
| 4,703,761 A | 11/1987 | Rathbone et al. |
| 4,727,020 A | 2/1988 | Recktenwald |
| 4,751,188 A | 6/1988 | Valet |
| 4,769,150 A | 9/1988 | Ramstack |
| 4,857,735 A | 8/1989 | Noller |
| 4,959,305 A | 9/1990 | Woodrum |
| 5,014,718 A | 5/1991 | Mitchen |
| 5,053,626 A | 10/1991 | Tillotson |
| 5,073,857 A | 12/1991 | Peters et al. |
| 5,102,625 A | 4/1992 | Milo |
| 5,134,662 A | 7/1992 | Bacus et al. |
| 5,159,642 A | 10/1992 | Kosaka |
| 5,187,749 A | 2/1993 | Sugimoto et al. |
| 5,196,709 A | 3/1993 | Berndt et al. |
| 5,200,152 A | 4/1993 | Brown |
| 5,294,799 A | 3/1994 | Aslund et al. |
| 5,332,905 A | 7/1994 | Brooker et al. |
| 5,348,859 A | 9/1994 | Brunhouse et al. |
| 5,385,539 A | 1/1995 | Maynard |
| 5,423,738 A * | 6/1995 | Robinson ............ A61M 1/34 604/28 |
| 5,489,771 A | 2/1996 | Beach et al. |
| 5,491,343 A | 2/1996 | Brooker |
| 5,528,045 A | 6/1996 | Hoffman et al. |
| 5,547,849 A | 8/1996 | Baer et al. |
| 5,556,764 A | 9/1996 | Sizto et al. |
| 5,592,291 A | 1/1997 | Iida |
| 5,599,668 A | 2/1997 | Stimpson et al. |
| 5,627,037 A | 5/1997 | Ward et al. |
| 5,661,558 A | 8/1997 | Nogami et al. |
| 5,674,457 A | 10/1997 | Williamsson et al. |
| 5,675,155 A | 10/1997 | Pentoney, Jr. et al. |
| 5,681,529 A | 10/1997 | Taguchi et al. |
| 5,692,503 A | 12/1997 | Kuenstner |
| 5,732,150 A | 3/1998 | Zhou et al. |
| 5,733,721 A | 3/1998 | Hemstreet, III et al. |
| 5,773,301 A | 6/1998 | Ziegler |
| 5,851,835 A | 12/1998 | Groner |
| 5,898,487 A | 4/1999 | Hage |
| 5,933,233 A | 8/1999 | Gunther |
| 5,938,439 A | 8/1999 | Merlins et al. |
| 6,043,880 A | 3/2000 | Andrews et al. |
| 6,045,699 A | 4/2000 | Yazawa et al. |
| 6,064,474 A | 5/2000 | Lee et al. |
| 6,064,897 A | 5/2000 | Lindberg et al. |
| 6,094,592 A | 7/2000 | Yorkey et al. |
| 6,103,197 A | 8/2000 | Werner |
| 6,154,282 A | 11/2000 | Lilge et al. |
| 6,159,740 A | 12/2000 | Hudson et al. |
| 6,181,418 B1 | 1/2001 | Palumbo et al. |
| 6,187,592 B1 | 2/2001 | Gourley |
| 6,214,629 B1 | 4/2001 | Freitag et al. |
| 6,226,347 B1 | 5/2001 | Golenhofen |
| 6,262,798 B1 | 7/2001 | Shepherd et al. |
| 6,294,094 B1 | 9/2001 | Muller et al. |
| 6,305,804 B1 | 10/2001 | Rice et al. |
| 6,342,376 B1 | 1/2002 | Kozian et al. |
| 6,350,613 B1 | 2/2002 | Wardlaw et al. |
| 6,410,341 B1 | 6/2002 | Freitag et al. |
| 6,453,060 B1 | 9/2002 | Riley et al. |
| 6,477,394 B2 | 11/2002 | Rice et al. |
| 6,479,299 B1 | 11/2002 | Parce et al. |
| 6,493,567 B1 | 12/2002 | Krivitski et al. |
| 6,519,025 B2 | 2/2003 | Shepherd et al. |
| 6,563,585 B1 | 5/2003 | Rao et al. |
| 6,589,749 B1 * | 7/2003 | Guirguis ............ A61B 10/007 210/321.6 |
| 6,594,075 B1 | 7/2003 | Kanao et al. |
| 6,611,320 B1 | 8/2003 | Lindberg et al. |
| 6,612,111 B1 | 9/2003 | Hodges et al. |
| 6,638,769 B2 | 10/2003 | Lilja et al. |
| 6,665,060 B1 | 12/2003 | Zahniser et al. |
| 6,696,240 B1 | 2/2004 | Kloepfer et al. |
| 6,716,588 B2 | 4/2004 | Sammak et al. |
| 6,723,290 B1 | 4/2004 | Wardlaw |
| 6,740,527 B1 | 5/2004 | Wong et al. |
| 6,825,921 B1 | 11/2004 | Modlin et al. |
| 6,828,567 B2 | 12/2004 | Amirkhanian et al. |
| 6,831,733 B2 | 12/2004 | Pettersson et al. |
| 6,858,400 B2 | 2/2005 | Bristow |
| 6,862,534 B2 | 3/2005 | Sterling et al. |
| 6,869,570 B2 | 3/2005 | Wardlaw |
| 6,898,458 B2 | 5/2005 | Zeng et al. |
| 6,960,165 B2 | 11/2005 | Ueno et al. |
| 6,985,224 B2 | 1/2006 | Hart |
| 6,999,173 B2 | 2/2006 | Kleinfeld et al. |
| 7,075,628 B2 | 7/2006 | Shepherd et al. |
| 7,094,562 B2 | 8/2006 | Bittner |
| 7,096,124 B2 | 8/2006 | Sterling et al. |
| 7,115,841 B2 | 10/2006 | Zeng et al. |
| 7,133,545 B2 | 11/2006 | Douglass et al. |
| 7,146,372 B2 | 12/2006 | Bacus et al. |
| 7,149,332 B2 | 12/2006 | Bacus et al. |
| 7,271,912 B2 | 9/2007 | Sterling et al. |
| 7,279,134 B2 | 10/2007 | Chan et al. |
| 7,303,922 B2 | 12/2007 | Jeng et al. |
| 7,319,894 B2 | 1/2008 | Higgins |
| 7,324,674 B2 | 1/2008 | Ozawa et al. |
| 7,420,660 B2 | 9/2008 | Muller |
| 7,426,407 B2 | 9/2008 | Higgins |
| 7,477,382 B2 | 1/2009 | Grey et al. |
| 7,515,268 B1 | 4/2009 | Ayliffe et al. |
| 7,518,727 B2 | 4/2009 | Pentoney, Jr. et al. |
| 7,539,335 B2 | 5/2009 | Fukuyama |
| 7,560,073 B1 | 7/2009 | Peters et al. |
| 7,625,712 B2 | 12/2009 | Paul et al. |
| 7,630,063 B2 | 12/2009 | Padmanabhan et al. |
| 7,674,598 B2 | 3/2010 | Paul et al. |
| 7,738,094 B2 | 6/2010 | Goldberg |
| 7,762,946 B2 | 7/2010 | Sugimoto |
| 7,781,226 B2 | 8/2010 | McDevitt et al. |
| 7,790,464 B2 | 9/2010 | Tarasev |
| 7,816,135 B2 | 10/2010 | Goldberg |
| 7,826,728 B2 | 11/2010 | Konno et al. |
| 7,854,891 B2 | 12/2010 | Yamamoto et al. |
| 7,892,551 B2 | 2/2011 | Glencross |
| 7,903,241 B2 | 3/2011 | Wardlaw et al. |
| 7,952,692 B2 | 5/2011 | Primack et al. |
| 8,009,894 B2 | 8/2011 | Lindberg et al. |
| 8,125,623 B2 | 2/2012 | Munger et al. |
| 8,224,058 B2 | 7/2012 | Lindberg et al. |
| 8,244,021 B2 | 8/2012 | Lett et al. |
| 8,306,594 B2 | 11/2012 | Paseman et al. |
| 8,353,848 B2 | 1/2013 | Long et al. |
| 8,377,398 B2 | 2/2013 | McDevitt et al. |
| 8,406,859 B2 | 3/2013 | Zuzak et al. |
| 8,483,789 B2 | 7/2013 | Higgins |

(56) References Cited

U.S. PATENT DOCUMENTS

| | | |
|---|---|---|
| 8,488,903 B2 | 7/2013 | Higuchi |
| 8,541,227 B2 | 9/2013 | Christensen et al. |
| 2002/0096468 A1 | 7/2002 | Zuk, Jr. |
| 2003/0152927 A1 | 8/2003 | Jakobsen et al. |
| 2003/0170613 A1 | 9/2003 | Straus |
| 2003/0206828 A1 | 11/2003 | Bell |
| 2003/0230728 A1 | 12/2003 | Dai et al. |
| 2004/0224329 A1 | 11/2004 | Gjerde et al. |
| 2005/0054949 A1* | 3/2005 | McKinnon .......... A61B 5/15003 600/576 |
| 2005/0142565 A1 | 6/2005 | Samper et al. |
| 2005/0190058 A1 | 9/2005 | Call |
| 2006/0020531 A1 | 1/2006 | Veeneman et al. |
| 2006/0024756 A1 | 2/2006 | Tibbe et al. |
| 2006/0029923 A1* | 2/2006 | Togawa ................ B01D 61/18 435/2 |
| 2006/0060531 A1 | 3/2006 | Coville et al. |
| 2006/0241495 A1 | 10/2006 | Kurtz |
| 2006/0252079 A1 | 11/2006 | Oldham et al. |
| 2007/0132994 A1 | 6/2007 | Kobayashi et al. |
| 2007/0178009 A1 | 8/2007 | Sakaino et al. |
| 2007/0189923 A1 | 8/2007 | Lenhard et al. |
| 2008/0190220 A1 | 8/2008 | Backes et al. |
| 2008/0203319 A1 | 8/2008 | Pentoney et al. |
| 2008/0268469 A1 | 10/2008 | Srienc et al. |
| 2009/0075324 A1 | 3/2009 | Pettersson |
| 2009/0107903 A1* | 4/2009 | Dassa .................. B01L 3/5021 210/206 |
| 2009/0181411 A1 | 7/2009 | Battrell et al. |
| 2009/0259145 A1* | 10/2009 | Bartfeld .............. A61B 5/1405 600/576 |
| 2010/0291599 A1 | 11/2010 | Tague, Jr. et al. |
| 2011/0034882 A1 | 2/2011 | Quinn et al. |
| 2011/0118139 A1 | 5/2011 | Mehta et al. |
| 2011/0159457 A1* | 6/2011 | Offermann ............ A61B 5/417 433/91 |
| 2011/0313143 A1* | 12/2011 | Martin ................. B01L 3/5021 536/23.1 |
| 2012/0016307 A1 | 1/2012 | Burkholz et al. |
| 2012/0123297 A1 | 5/2012 | Brancazio |
| 2012/0253291 A1 | 10/2012 | Ivosevic et al. |
| 2013/0045529 A1 | 2/2013 | Goldberg et al. |
| 2013/0162990 A1 | 6/2013 | Kobayashi et al. |
| 2014/0093896 A1 | 4/2014 | Mongale et al. |
| 2014/0200154 A1 | 7/2014 | Sugarman et al. |
| 2015/0125882 A1 | 5/2015 | Bornheimer et al. |
| 2015/0132789 A1 | 5/2015 | Bornheimer et al. |
| 2017/0067807 A1* | 3/2017 | Simon ................ A61B 5/15003 |
| 2017/0343455 A1* | 11/2017 | Middleton ........... G01N 1/4077 |

FOREIGN PATENT DOCUMENTS

| | | |
|---|---|---|
| EP | 0663070 A1 | 7/1995 |
| EP | 0681177 A1 | 11/1995 |
| EP | 0737855 A1 | 10/1996 |
| EP | 0744600 A1 | 11/1996 |
| EP | 0788615 A1 | 8/1997 |
| EP | 0800074 A1 | 10/1997 |
| EP | 0818682 A2 | 1/1998 |
| EP | 0821784 B1 | 11/1998 |
| EP | 0959346 A2 | 11/1999 |
| EP | 0969279 A2 | 1/2000 |
| EP | 0809807 B1 | 7/2002 |
| EP | 1324021 A1 | 7/2003 |
| EP | 1347702 A2 | 10/2003 |
| EP | 1456649 B1 | 6/2006 |
| EP | 1698883 A1 | 9/2006 |
| EP | 1701150 A1 | 9/2006 |
| EP | 1767935 A1 | 3/2007 |
| EP | 1924195 A2 | 5/2008 |
| EP | 1990638 A1 | 11/2008 |
| EP | 2016390 A1 | 1/2009 |
| EP | 2041549 A1 | 4/2009 |
| EP | 2083687 A1 | 8/2009 |
| EP | 1405073 B1 | 3/2010 |
| EP | 2232442 A1 | 9/2010 |
| EP | 2016390 B1 | 4/2013 |
| EP | 2586370 A2 | 5/2013 |
| EP | 2605020 A2 | 6/2013 |
| EP | 1558934 B1 | 7/2013 |
| EP | 2676606 A1 | 12/2013 |
| GB | 1260103 | 1/1972 |
| JP | 200188098 A | 4/2001 |
| JP | 2002506208 A | 2/2002 |
| JP | 2002516982 A | 6/2002 |
| JP | 2008525768 A | 7/2008 |
| WO | 8500524 | 2/1985 |
| WO | 9311221 A1 | 6/1993 |
| WO | 9624425 A1 | 8/1996 |
| WO | 9920998 A1 | 4/1999 |
| WO | 9945384 A1 | 9/1999 |
| WO | 0028297 A2 | 5/2000 |
| WO | 0029847 A2 | 5/2000 |
| WO | 0244729 A1 | 6/2002 |
| WO | 0250518 A2 | 6/2002 |
| WO | 03036290 A1 | 5/2003 |
| WO | 2004100887 A2 | 11/2004 |
| WO | 2005100539 A2 | 10/2005 |
| WO | 2006047831 A1 | 5/2006 |
| WO | 2006096126 A1 | 9/2006 |
| WO | 2006119368 A2 | 11/2006 |
| WO | 2007012975 A1 | 2/2007 |
| WO | 2007033318 A2 | 3/2007 |
| WO | 2007051861 A1 | 5/2007 |
| WO | 2007111555 A1 | 10/2007 |
| WO | 2007129948 A1 | 11/2007 |
| WO | 2008002462 A2 | 1/2008 |
| WO | 2008010761 A1 | 1/2008 |
| WO | 2008037068 A1 | 4/2008 |
| WO | 2008103992 A2 | 8/2008 |
| WO | 2009091318 A1 | 7/2009 |
| WO | 2009155612 A2 | 12/2009 |
| WO | 2010003518 A1 | 1/2010 |
| WO | 2010085658 A1 | 7/2010 |
| WO | 2011133540 A2 | 10/2011 |
| WO | 2012122088 A1 | 9/2012 |
| WO | 2013075031 A1 | 5/2013 |
| WO | 2014095058 A1 | 6/2014 |
| WO | 2015014934 A1 | 2/2015 |

OTHER PUBLICATIONS

Advantec MFS et al., Vacuum Filtration, 2004, pp. 77-96.

Jensen, The Hirsch and Buchner Filtration Funnels, Journal of Chemical Education, 2006, vol. 83, No. 1283, pp. 1-2.

* cited by examiner

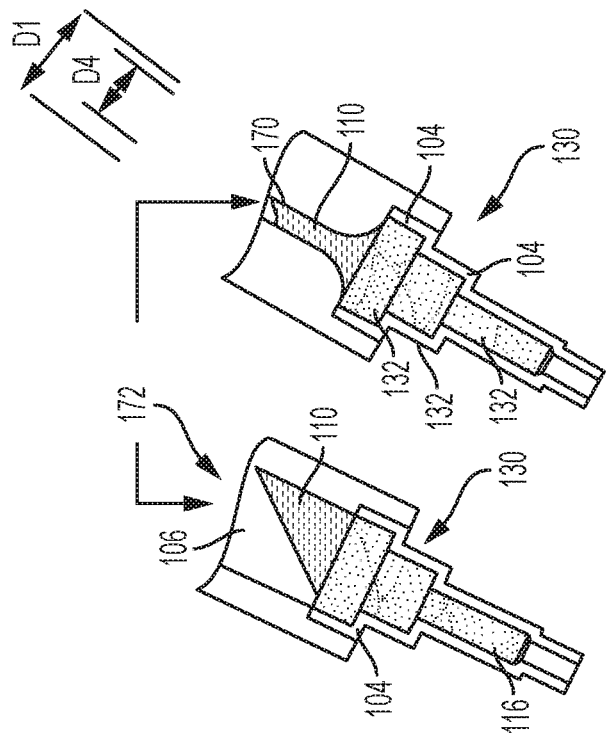
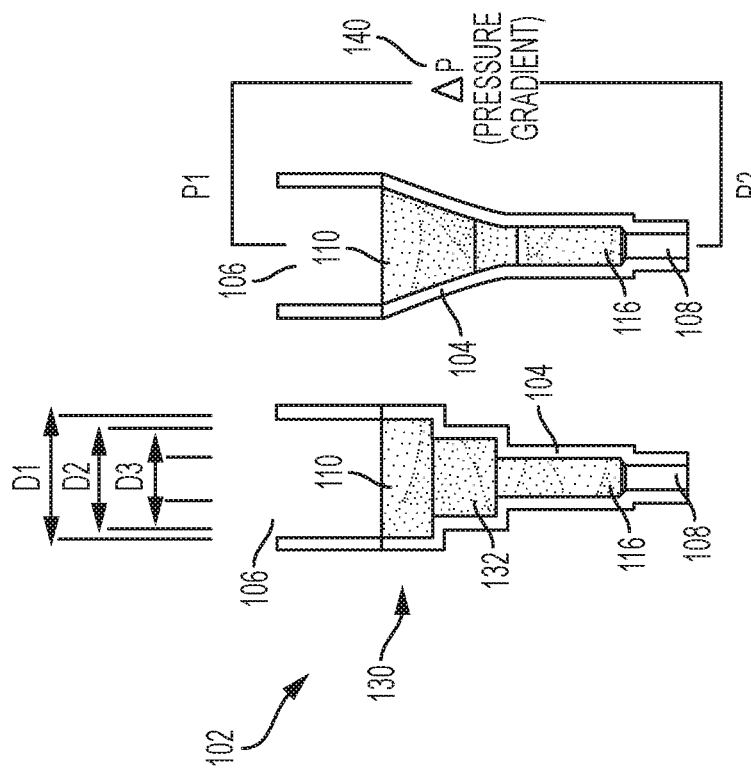
FIG. 7A    FIG. 7B
FIG. 6A    FIG. 6B

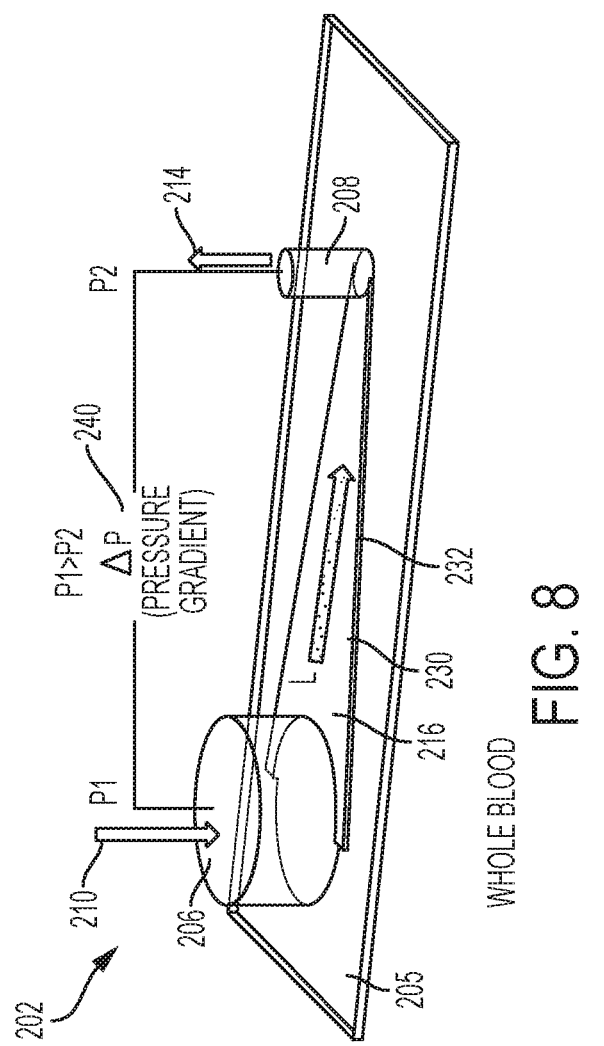

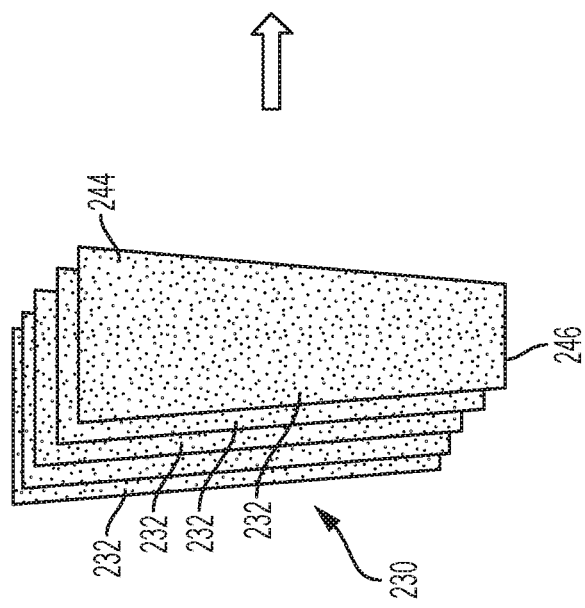
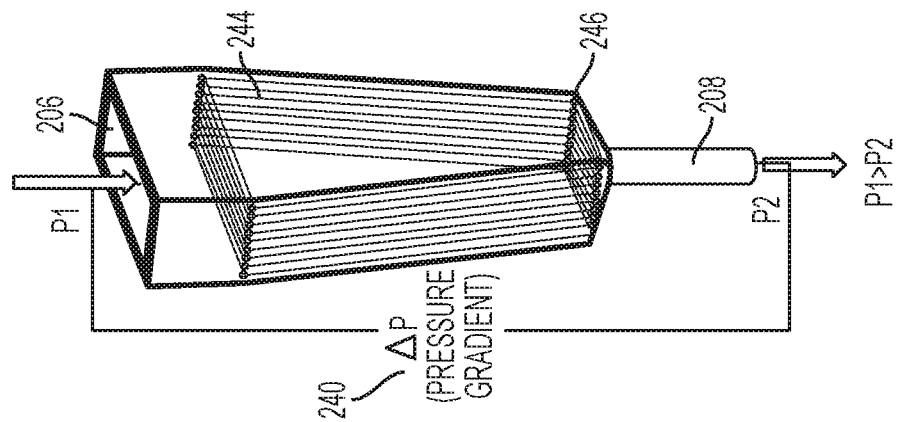
FIG. 9

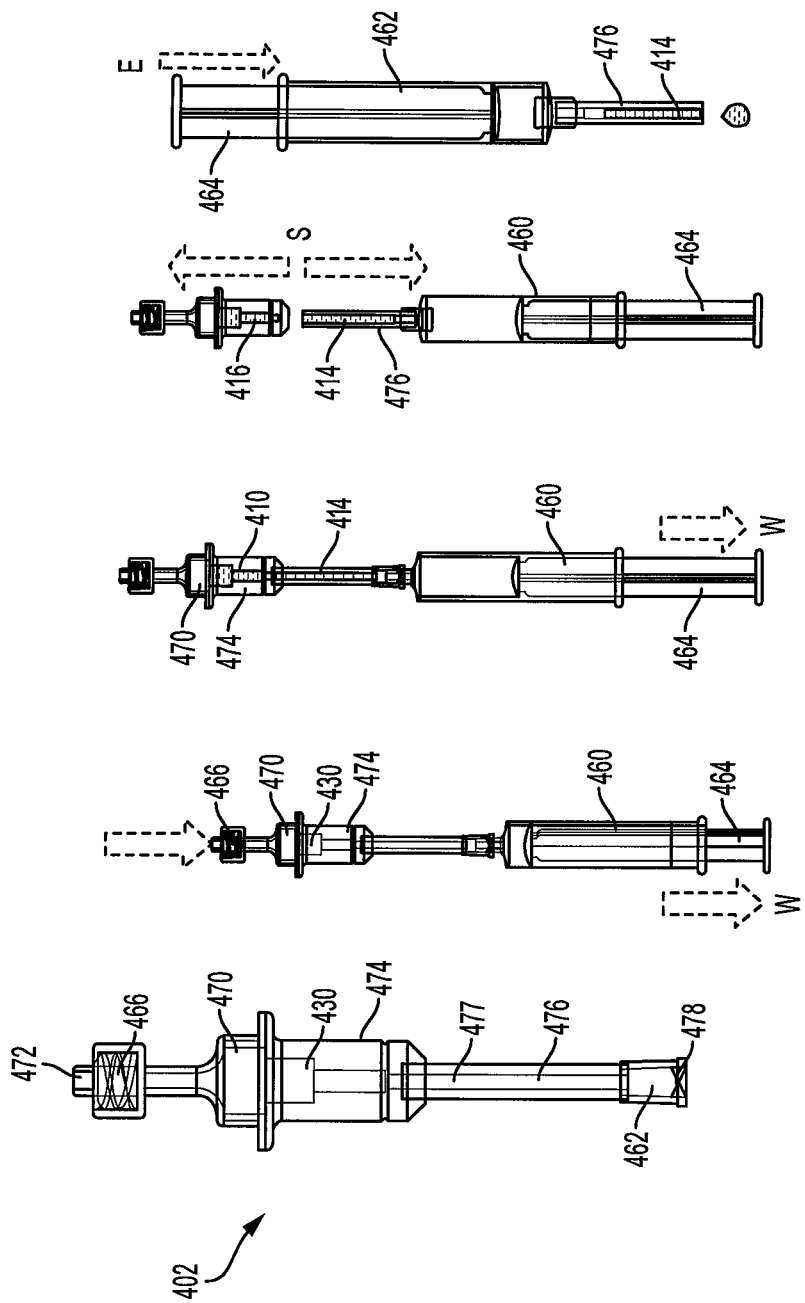

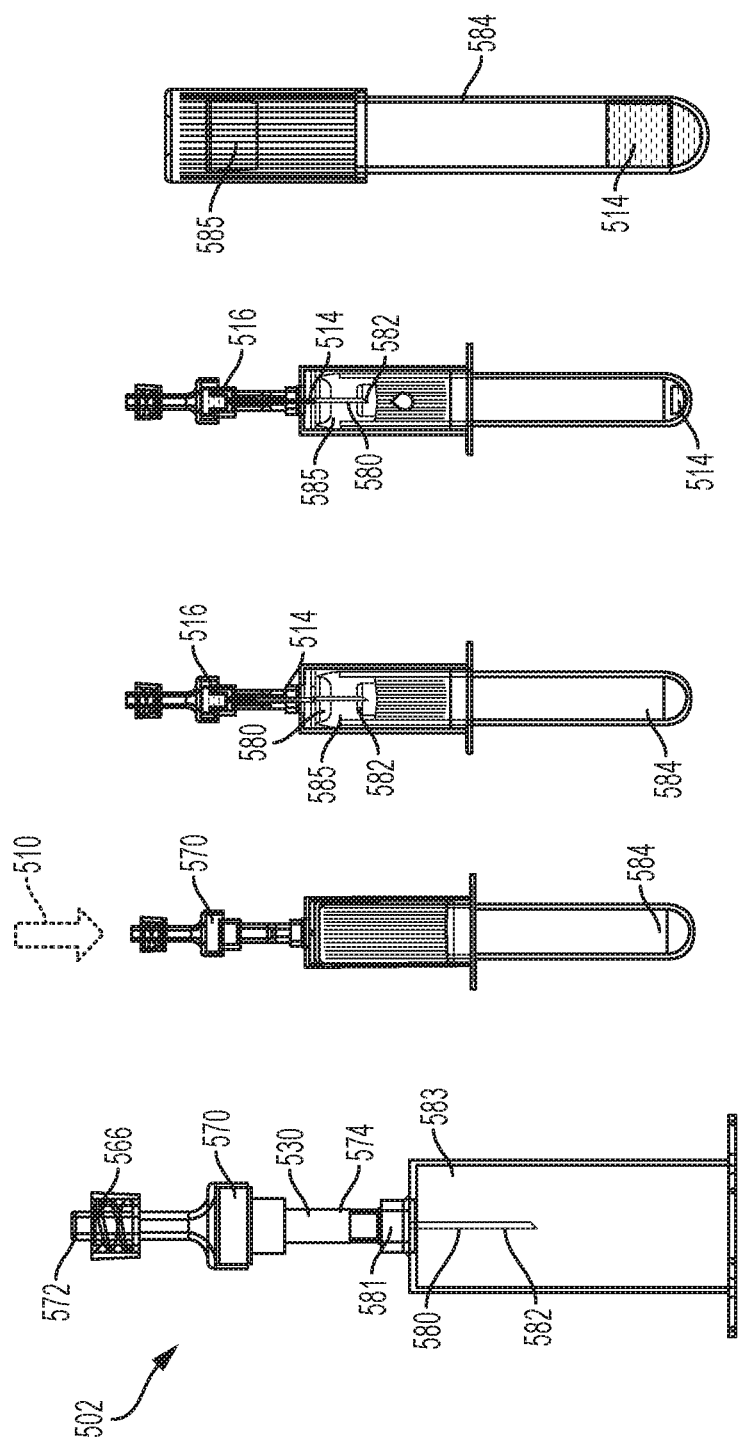

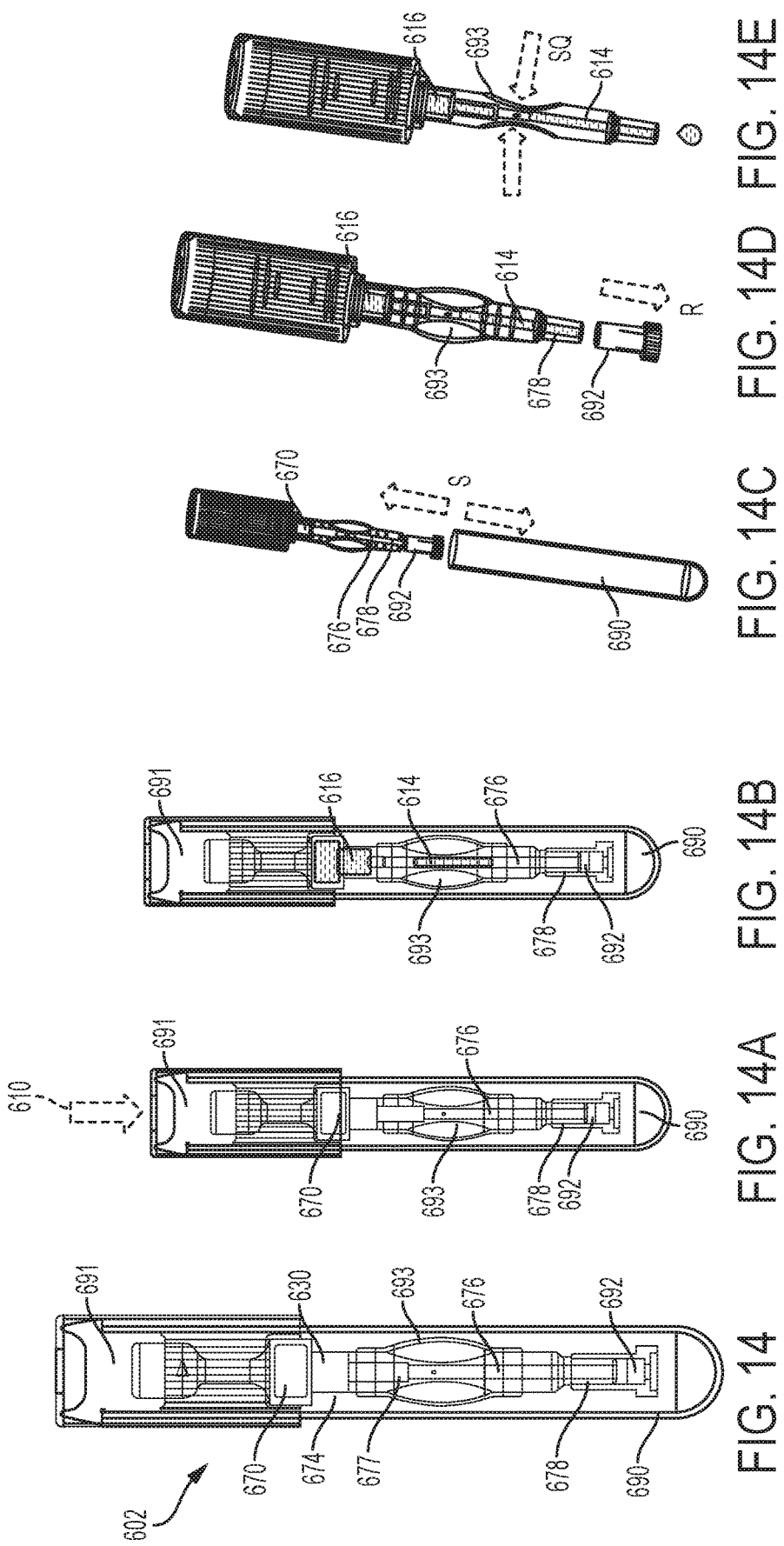

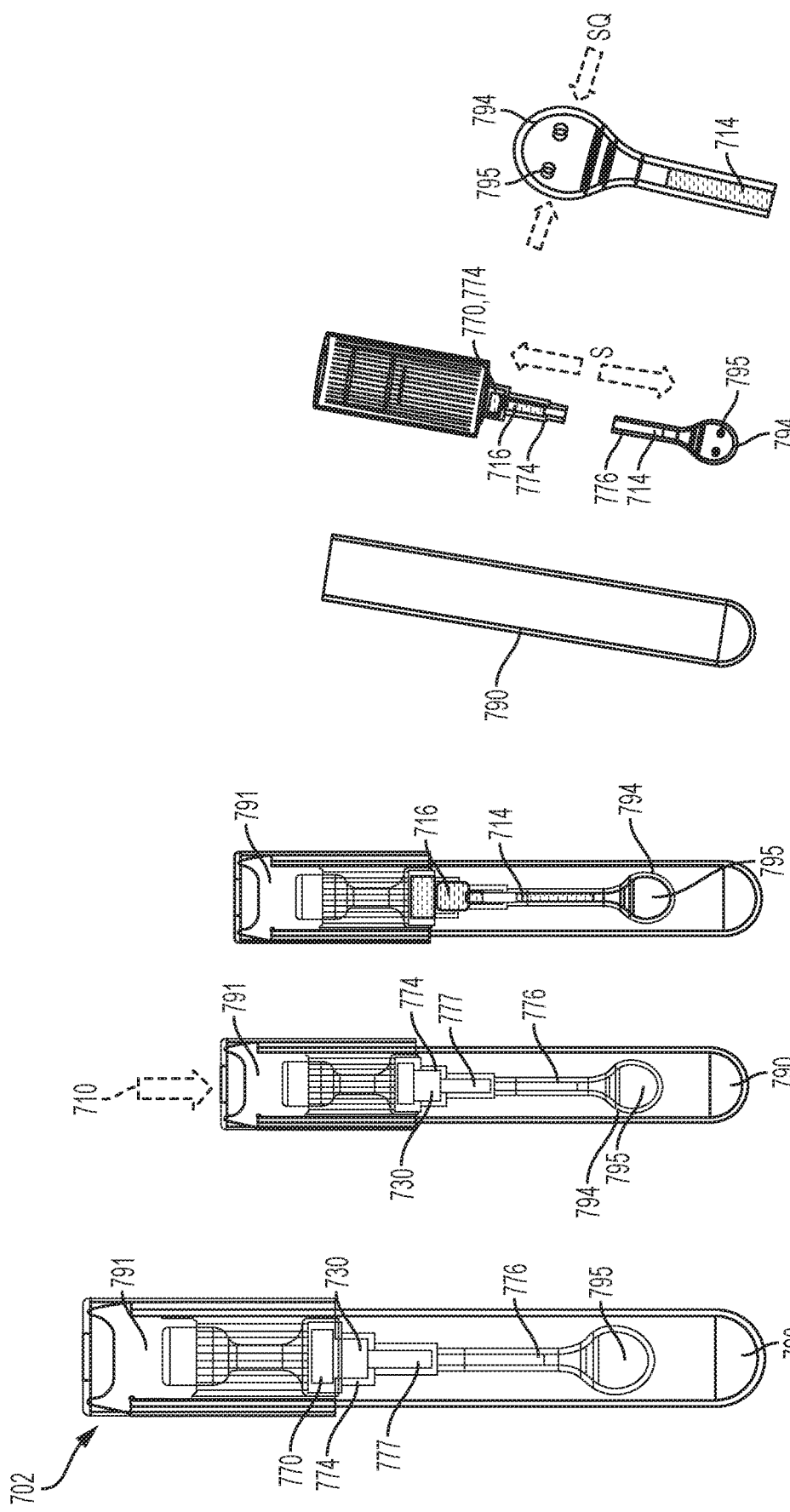

US 10,578,606 B2

DEPTH FILTRATION DEVICE FOR SEPARATING SPECIMEN PHASES

CROSS-REFERENCE TO RELATED APPLICATION

The present application claims priority to U.S. Provisional Application Ser. No. 62/212,797, filed Sep. 1, 2015, entitled "Depth Filtration Technology for Separating Plasma from Whole Blood", the entire disclosure of which is hereby incorporated by reference.

BACKGROUND OF THE INVENTION

Field of the Invention

The present disclosure relates generally to a device and method for separating higher and lower density fractions of a fluid sample and, more particularly, the present disclosure relates to a device and method for rapidly separating higher and lower density fractions of a fluid sample without the need for a centrifuge or other high-cost equipment.

Description of Related Art

Diagnostic tests may require separation of a patient's whole blood sample into components, such as serum or plasma (the lower density phase components), and particles and aggregates such as red and white blood cells and platelets (the higher density phase components). Samples of whole blood are typically collected via venipuncture through a cannula or needle attached to a syringe or an evacuated blood collection tube. After collection, separation of the blood into serum or plasma and blood cells is typically accomplished by centrifugation of the whole blood. More recently, there has been an effort to separate plasma using microfluidics. However, these approaches are limited by requirements of dilution and the total volume of blood that can be processed.

Another common method used for processing micro samples of blood is the lateral flow separation method wherein a blood sample moves through a strip of filter material in a lateral direction. However, the total surface area to volume requirements of the material, when using this method, limits the total volume of blood that can be processed.

Another technique for separating plasma from a whole blood sample is simple filtration which allows the blood sample to flow via capillary forces through a filter wherein the filter includes pore sizes which are smaller than the size of the cellular particles or red blood cells. This method is commonly referred to as conventional size exclusion filtration. In this method, the filter traps the cellular particles or red blood cells so as to separate these particles/cells from the serum or plasma portion. However, one drawback to this method is that the filter can become blocked, thus hindering movement of the whole blood sample therethrough and, thus, slowing and/or reducing the collection of the plasma portion of the sample.

SUMMARY OF THE INVENTION

The present disclosure provides a biological fluid collection device, such as a blood collection device, that is adapted to receive a multi-component blood sample having a cellular portion and a plasma portion and quickly, efficiently, and cost-effectively separate the plasma portion from the sample.

In accordance with one aspect of the invention, a device for separation of a biological sample into a first phase and a second phase includes a container including an inlet and an outlet wherein the inlet is configured for receiving the biological sample. The device further includes a separator located within the container for separating the biological sample into the first phase and the second phase. The separator can include a series of filters of variable pore sizes or multiple grades of fibrous filters to progressively filter out different cell types to yield a clean first phase and a member for creating a pressure gradient across the separator to increase a rate of movement of the biological sample through the separator such that the first phase exits the separator prior to the second phase.

According to one embodiment, at least one of the fibrous filters can include a chaotic fibrous structure that slows particles located within the second phase to further slow the flow of the second phase and increase a flow of the first phase through the separator.

The biological sample can move through the container in a vertical direction and the separator can include an open cell foam positioned adjacent the inlet. The device can further include a cell filter located after the separator wherein the cell filter is configured to block the second phase from movement therethrough and exiting through the outlet.

In accordance with one embodiment, a dry anticoagulant material can be deposited on the separator. The separator can also be treated to include at least one of a hydrophobic, hydrophilic, or reactive internal pore surface. Additionally, the separator can be treated to avoid analyte bias. This treatment can be either additive coatings that act to block analytes from sticking to a surface or chemical surface modifications.

The pressure gradient can include a first pressure located at an inlet of the container and a second pressure located at the outlet of the container and wherein the first pressure is greater than the second pressure. The member for creating the pressure gradient can include a pressure regulator for controlling the pressure gradient to generate a desired pressure profile. Depending upon which device is being used to create the pressure gradient, the pressure gradient can be one of, or a combination of, a constant, increasing, or decreasing pressure.

According to another aspect of the invention, a device for separation of a biological sample into a first phase and a second phase includes a container including at least a first portion having a first diameter, a second portion having a second diameter, and a third portion having a third diameter, an inlet located adjacent the first portion wherein the inlet is configured for receiving the biological sample, and an outlet located adjacent the third portion, wherein the second portion is located between the first and third portion. The device further includes a separator located within the container for separating the biological sample into the first phase and the second phase and a device for creating a pressure gradient across the separator to increase a rate of movement of the biological sample through the separator such that the first phase exits the separator and the outlet prior to the second phase, and wherein the first, second, and third diameters progressively decrease in size.

According to one design, the biological sample moves through the container in a vertical direction and at least one of the first, second, and third portions has a conical or tapered structure. The device can also include a narrow feed channel having a diameter which is less than the first diameter of the first portion.

According to another aspect of the invention, a device for separation of a biological sample into a first phase and a second phase includes a holder including an inlet and an outlet. The inlet is configured for receiving the biological sample. The device further includes at least one lateral flow strip cooperating with the holder for separating the biological sample into the first phase and the second phase and a member for creating a pressure gradient across the lateral flow strip to increase a rate of movement of the biological sample through the lateral flow strip such that the first phase exits the flow strip and the outlet prior to the second phase. The at least one lateral flow strip can comprise a plurality of lateral flow strips stacked one upon another. According to one embodiment, the lateral flow strips can have a trapezoidal shape having a large base and a small base wherein the large base is positioned adjacent the inlet of the holder and the small base is positioned adjacent the outlet of the holder.

According to yet another aspect of the invention, a device for the collection and separation of a biological sample into a first phase and a second phase includes a capillary tube configured for receiving the biological sample via capillary pressure, a container associated with the capillary tube wherein the container includes an outlet, a separator located within the container for separating the biological sample into the first phase and the second phase, and a member associated with the container outlet for creating a pressure gradient across the separator to increase a rate of movement of the biological sample through the separator to facilitate separation of the first phase from the second phase.

The separator can include at least one filter formed of a fibrous material. The member for creating the pressure gradient can comprise a syringe. The container can also comprise a separation chamber and a first phase collection chamber and wherein after separation of the sample and collection of the first phase into the collection chamber, the collection chamber can be removed from the separation chamber. According to one embodiment, the collection chamber can include a luer lock for connecting the collection chamber to the syringe and after removal of the collection chamber from the separation chamber, the syringe can be used to force the first phase out of the collection chamber and into a separate container for diagnostic testing.

According to still another aspect, a device for the collection of a biological sample and separation of the biological sample into a first phase and a second phase includes a collection chamber having an inlet for collecting the biological sample via venous pressure, a separation chamber associated with the collection chamber, a separator located within the separation chamber for separating the biological sample into the first phase and the second phase, a capillary tube associated with the separation chamber wherein the capillary tube includes a first end configured for receiving the first phase and a second end, and a member associated with the second end of the capillary tube for creating a pressure gradient across the separator to increase a rate of movement of the biological sample through the separator to facilitate separation of the first phase from the second phase.

According to one embodiment, the separator can comprise at least one filter formed of a fibrous material, and the member for creating the pressure gradient can comprise a syringe.

The capillary tube is separable from the separation chamber such that after separation of the sample and collection of the first phase into the capillary tube, the capillary tube can be removed from the separation chamber. The collection chamber can include a luer lock for connecting the collection chamber to a biological collection system, and the second end of the capillary tube can include a luer lock for connecting to the syringe.

According to still another aspect of the invention, a device for the collection of a biological sample and separation of the biological sample into a first phase and a second phase includes a collection chamber having an inlet for collecting the biological sample via venous pressure, a separation chamber associated with the collection chamber, a separator located within the separation chamber for separating the biological sample into the first phase and the second phase, a cannula having a first end associated with the separation chamber, and a vacuum tube associated with the separation chamber via a second end of the cannula. The vacuum tube can be configured for applying a pressure gradient across the separator to increase a rate of movement of the biological sample through the separator to facilitate separation of the first phase from the second phase and to cause the first phase to enter into the vacuum tube via the cannula.

According to one embodiment, the separator can comprise at least one filter formed of a fibrous material. The collection chamber and the separation chamber are separable from the vacuum tube such that after separation of the sample and collection of the first phase into the vacuum tube, the collection chamber and separation chamber can be removed from the vacuum tube. The collection chamber can include a luer lock for connecting the collection chamber to a biological collection system.

According to another aspect of the invention, a device for the collection of a biological sample and separation of the biological sample into a first phase and a second phase includes a sample collection chamber having an inlet for collecting the biological sample, a separation chamber associated with the sample collection chamber, a separator located within the separation chamber for separating the biological sample into the first phase and the second phase, a first phase collection chamber having a first end associated with the separation chamber, and a vacuum tube associated with the first phase collection chamber. The vacuum tube is configured for applying a pressure gradient across the separator to increase a rate of movement of the biological sample through the separator to facilitate separation of the first phase from the second phase and to cause the first phase to enter into the first phase collection chamber.

The vacuum tube can enclose at least a portion of the first phase collection chamber. The device can further include a vented closure associated with a second end of the first phase collection chamber. This vented closure is configured for providing fluid communication between the vacuum tube and the first phase collection chamber and to prevent collected first phase to exit the collection chamber and to enter the vacuum tube (air pass—liquid stops at this vented tip cap).

According to one embodiment, the vented closure can comprise a removable vented tip cap (air pass—liquid stops). The first phase collection chamber can include a flexible membrane such that upon removal of the tip cap, application of a squeezing force to the flexible membrane expels the first phase out of the device.

According to another embodiment, the vented closure can comprise a flexible member including apertures extending therethrough. The first phase collection chamber is removable from the sample collection chamber such that upon removal of the first phase collection chamber from the sample collection chamber, application of a squeezing force to the flexible member expels the first phase out of the device.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIGS. 6A-6B are side schematic views of chromatographic depth filtration devices having various container designs in accordance with an embodiment of the invention.

FIG. 7A is a side schematic view of a chromatographic depth filtration device in which orientation of the container effects the filtration of the biological sample.

FIG. 7B is a side schematic view of a chromatographic depth filtration device in which orientation of the container does not affect the filtration of the biological sample.

FIG. 8 is a perspective view of a lateral flow separation device in accordance with an embodiment of the invention.

FIG. 9 is a schematic perspective view of the lateral flow separation device of FIG. 8 in accordance with an embodiment of the invention.

FIG. 12 is a side perspective view of a chromatographic depth filtration device for processing a venous biological sample in accordance with an embodiment of the invention.

FIGS. 12A-12D are sequential side perspective views of the separation of the biological sample using the device of FIG. 12 in accordance with an embodiment of the invention.

FIG. 13 is a side perspective view of a chromatographic depth filtration device for processing a venous biological sample in accordance with an embodiment of the invention.

FIGS. 13A-13D are sequential side perspective views of the separation of the biological sample using the device of FIG. 13 in accordance with an embodiment of the invention.

FIG. 14 is a side perspective view of a chromatographic depth filtration device for processing a venous biological sample in accordance with an embodiment of the invention.

FIGS. 14A-14E are sequential side perspective views of the separation of the biological sample using the device of FIG. 14 in accordance with an embodiment of the invention.

FIG. 15 is a side perspective view of a chromatographic depth filtration device for processing a venous biological sample in accordance with an embodiment of the invention.

FIGS. 15A-15D are sequential side perspective views of the separation of the biological sample using the device of FIG. 15 in accordance with an embodiment of the invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DESCRIPTION OF THE INVENTION

Figures 2A, 2B, 2C, 2D:
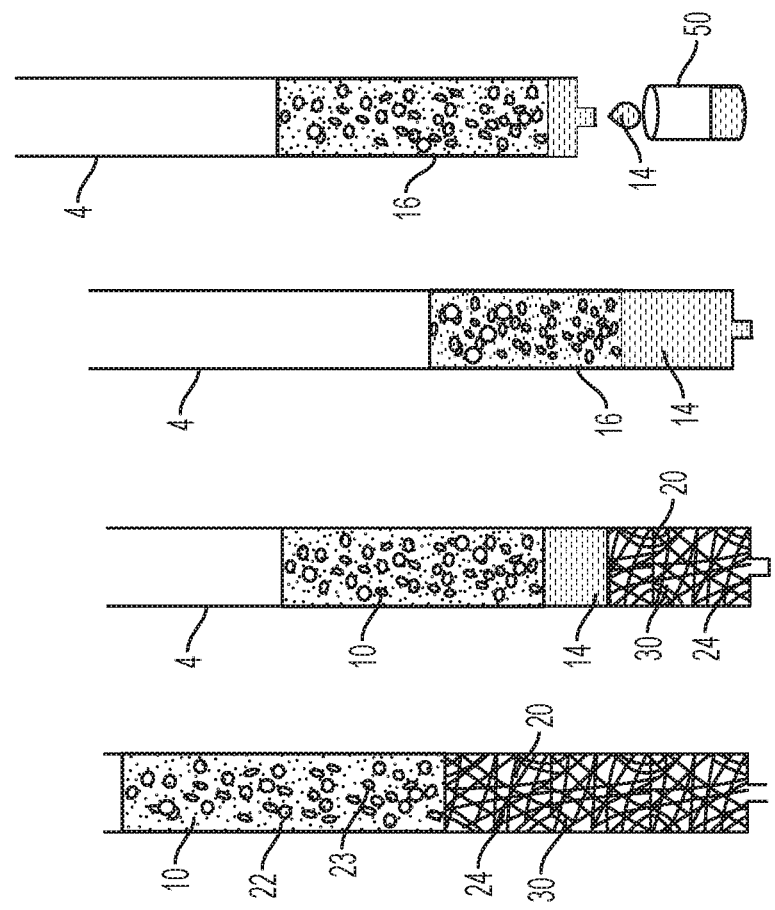
FIGS. 2A-2D are sequential side elevation views of a chromatographic depth filtration in accordance with an embodiment of the invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Figure 1:
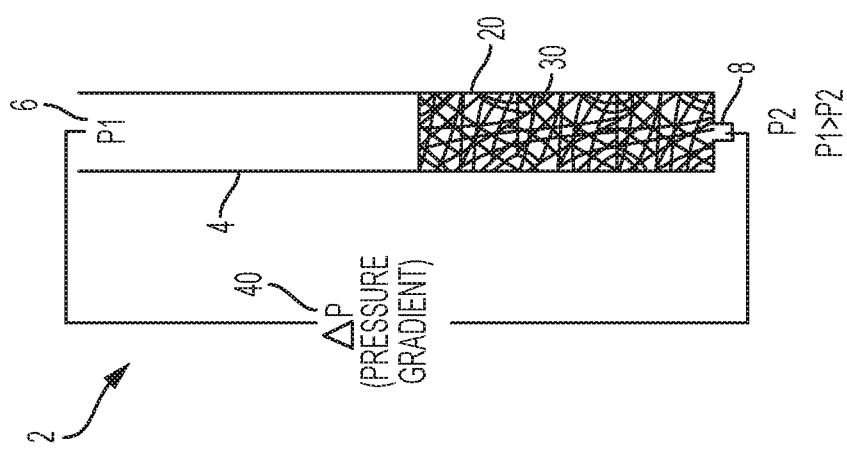
FIG. 1 is a side elevation view of a chromatographic depth filtration device.

Reference is made to FIGS. 1 and 2A-2D which show a device, generally indicated as 2, including a container 4, and a method for the sequential separation of a biological sample, such as a whole blood sample 10, into a first phase or plasma phase 14 and a second phase or cellular phase 16 using chromatographic depth filtration in accordance with the invention. Whole blood includes four components: red blood cells, white blood cells, plasma, and platelets. The liquid component of blood is plasma, which comprises a mixture of water, sugar, fat, protein, and salts. When whole blood is made to flow through a separator 30, such as a highly porous/fibrous material 20, the red blood cells 22 and other cellular particles, i.e., white blood cells, platelets, and the like 23 interact with fibers 24 either by colliding or wrapping around the fibers 24. This interaction slows the cellular particles 22, 23 within the cellular phase 16, whereas the plasma phase 14 moves ahead at a faster rate. Because of this phenomenon, a cell free plasma front or phase 14 is produced ahead of the cellular phase 16. This leading plasma front or phase 14 is then collected in a container 50 as it exits the separator 30, as shown in FIG. 2D, and sent for diagnostic testing. Typically, when the blood moves through the separator 30 via capillary pressure only, the cellular particles 22, 23 often block the openings of the separator 30, slowing down the separation process. In accordance with the present invention, a pressure gradient 40, as illustrated in FIG. 1, can be applied across the separator 30 to increase a rate of movement of the biological sample 12 through the separator 30 such that the first phase 14 moves through and exits the separator 30 prior to the second phase 16.

Figure 3:
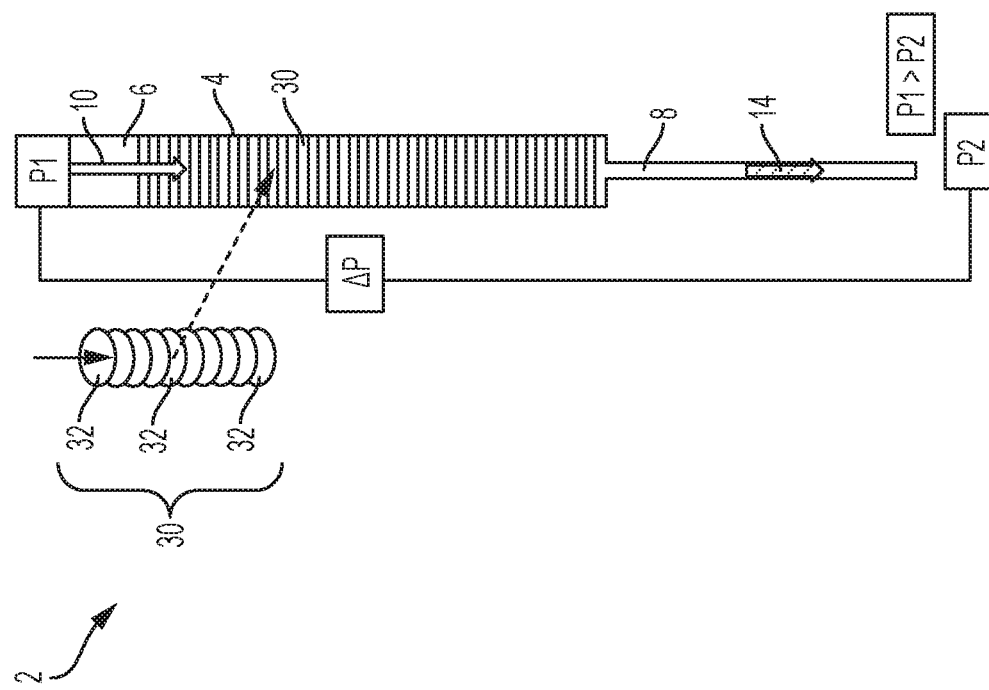
FIG. 3 is a side elevation view of a chromatographic depth filtration device in accordance with an embodiment of the invention.
Figure 4:
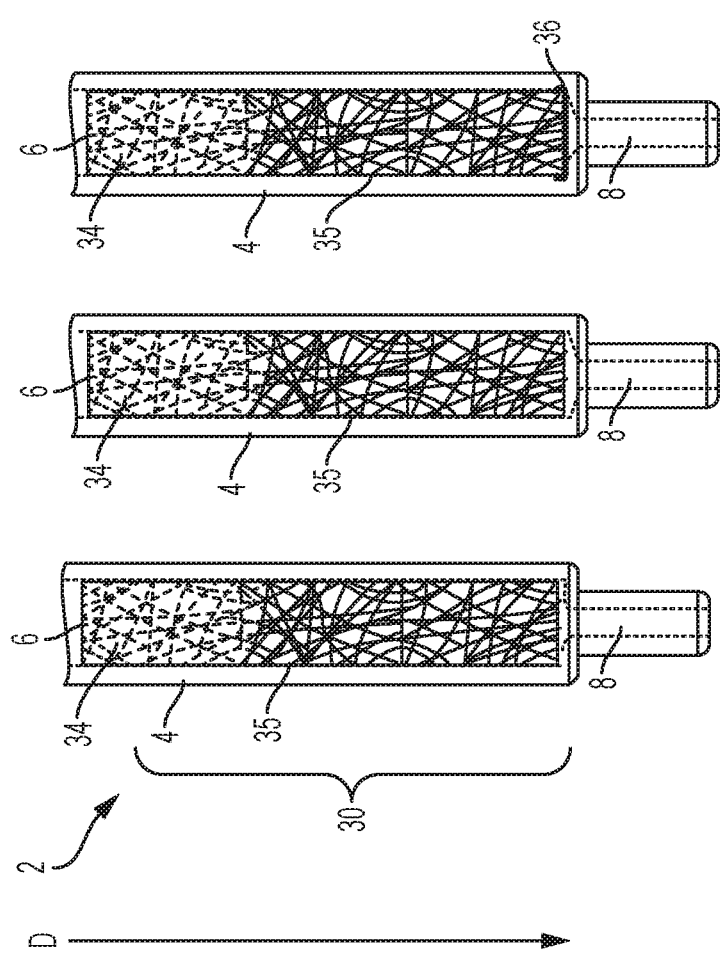
FIGS. 4A-4C are side elevation views of chromatographic depth filtration devices using various separation devices in accordance with an embodiment of the invention.
Figure 5:
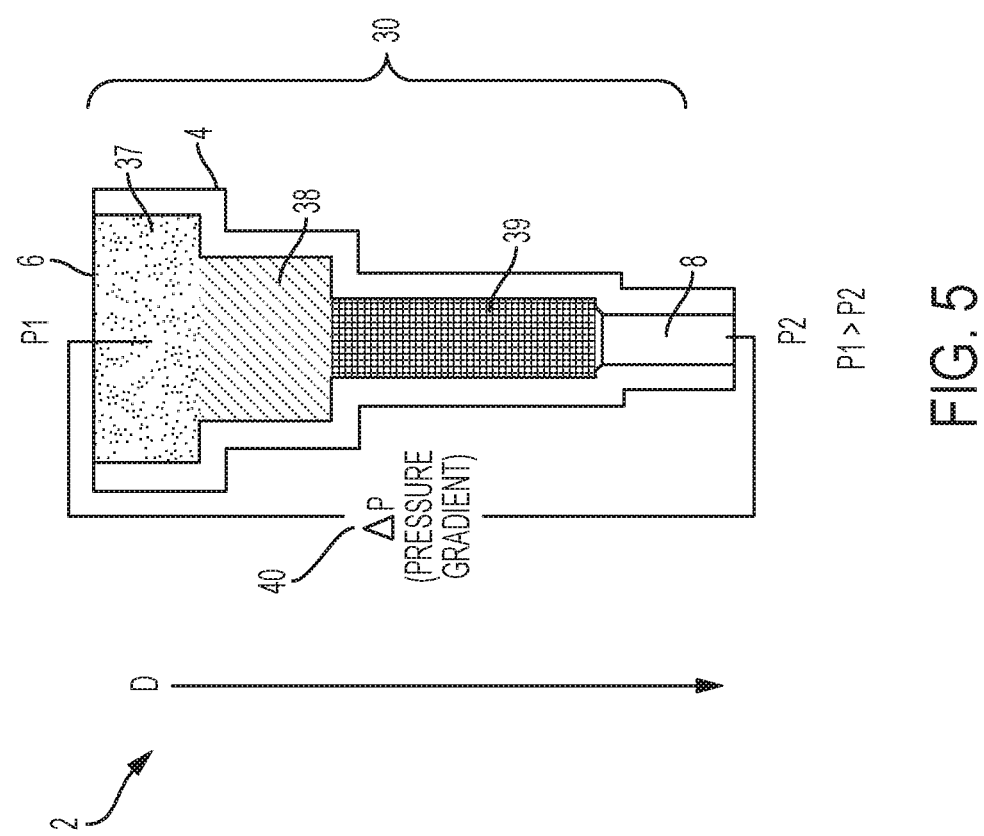
FIG. 5 is a side schematic view of a chromatographic depth filtration device including a multiple stage separation device in accordance with an embodiment of the invention-sectional schematic view of a chromatographic depth filtration device.

With continuing reference to FIGS. 1 and 2A-2D and with further reference to FIGS. 3, 4A-4C, and 5, the device 2 for separation of the biological sample 10 into a first phase 14 and a second phase 16 includes a container 4 including an inlet 6 and an outlet 8 wherein the inlet 6 is configured for receiving the biological sample 10. The device 2 further includes the separator 30 located within the container 4 for separating the biological sample 10 into the first phase 14 and the second phase 16. With particular reference to FIGS. 3, 4A-4C, and 5, the separator 30 can include a series of filters 32. According to one embodiment, at least one of the filters 32 can be a fibrous filter having a chaotic fibrous structure that slows and traps the red blood cells and cellular particles 22, 23 located within the second phase 16 to further slow the flow of the second phase 16 and increase the flow of the first phase 14 through the separator. The fibrous structure of the separator 30 is designed to slow down the flow of the blood cells by acting as flow obstacles which allow the plasma/serum or the first phase 14 to move faster through the separator 30 and therefore separate toward the front of the sample flow. According to one embodiment, the series of filters 32 can have the same porosity, as shown in FIG. 3. Alternatively, as shown in FIGS. 4A-4C, the separator 30 or series of filters 32 can have variable pore sizes through which the biological sample 10 moves in a vertical or descending direction wherein the pore size decreases in a downward direction D. For example, the series of filters 32 can include an open cell foam 34 positioned adjacent the inlet 6, a fibrous filter layer 35, and a cell capture filter 36 located after the separator 30 wherein the cell capture filter 36 is configured to block the second phase 16 from movement therethrough and exiting through the outlet 8. According to yet another embodiment as shown in FIG. 5, the separator 30 can include multiple stages filled with different grades of filters having variable pore sizes 37, 38, 39 to progressively filter out different cell types to yield a clean first phase 14.

Figure 10:
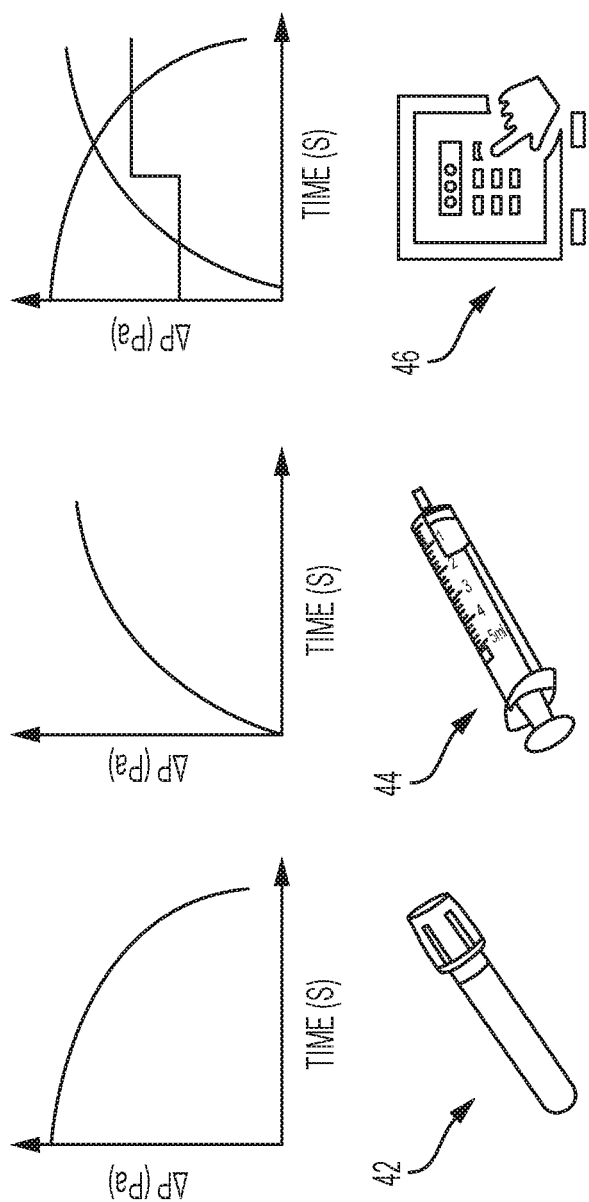
FIGS. 10A-10C are various pressure modes which can be used with the chromatographic depth filtration devices in accordance with an embodiment of the invention.

The device further includes a member for creating a pressure gradient 40 across the separator 30 and is provided to increase a rate of movement of the biological sample 12 through the separator 30 such that the first phase 14 exits the separator 30 prior to the second phase 16. The pressure gradient 40 can include a first pressure P1 located at the inlet 6 of the container 4 and a second pressure P2 located at the outlet 8 of the container 4 and wherein the first pressure P1 is greater than the second pressure P2. The member for creating the pressure gradient can include a pressure regulator (not shown) for controlling the pressure gradient to generate a desired pressure profile. As shown in FIGS. 10A-10C and discussed in further detail below, depending upon which device is being used to create the pressure gradient 40, the pressure gradient 40 can be one of a constant, increasing, or decreasing pressure.

The separator 30 can include a dry anticoagulant material deposited thereon. This can be done by a technique wherein the separator material is soaked in a liquid solution of the anticoagulant of desired concentration and then evaporating the liquid. In a similar way, the separation material can be treated to include at least one of a hydrophobic, hydrophilic, or reactive internal pore surface.

Additionally, the separator can be treated to avoid analyte bias. Analyte bias is the difference in measured value of analyte from a control value. Generally, biases occur because of analyte sticking to a surface, analytes leaching from the surface, introduction of other components interfering with the measurement, or activation of biological processes. In order to avoid potential analyte bias associated with the separator 30, the material of the separator 30 can be treated. This treatment generally falls into two categories: additive coatings that act to block analytes from sticking to a surface, and chemical surface modifications. Additive coatings can include, but are not limited to the following: (1) proteins like bovine serum albumin (BSA), casein, or non-fat milk; (2) surfactants such as polysorbate 20 (Tween 20) and organosilicone (L-720); (3) polymers and copolymers such as polyethylene glycol (PEG), polyvinyl alcohol (PVA), and polyvinylpyrrolidone (PVP); (4) carbohydrates such as dextran and glycosamino glycans like heparin; and (5) a cell membrane mimicking polymer like Lipidure, 2-methacryloyloxy ethyl phosphorylcholine. Chemical surface modifications can include, but are not limited to the following: (1) gas plasma treatment; (2) chemical bonding of polyethylene glycol (PEG) or other polymers to achieve a desired hydrophobicity or hydrophilicity; (3) chemical modification of the surface to introduce hydrophilic groups like ethylene glycol, or hydrophobic groups, such as long carbon chains; and (4) vapor deposition of a substance such as parylene. It can be appreciated that combinations of any of the above materials may be used to achieve the desired properties to minimize analyte bias for a specific analyte or group of analytes. In order to address the broadest range of analytes, a material/treatment combination resulting in a hydrophilic, neutral surface is targeted; however, the other treatments can be used for addressing specific analytes.

Reference is now made to FIGS. 6A-6B and 7A-7B, which show a device, generally indicated as 102 for separation of a biological sample 110 into a first phase 114 and a second phase 116 wherein a container 104 has a tapered, stepped, or conical structure which improves the separation time of the biological sample 110 and results in an increased surface area at an inlet 106 which allows for processing of a large volume of the biological sample 110. FIG. 5 also shows a stepped configuration for the container. The device 102 includes a container 104 having a first portion 160 having a first diameter D1, a second portion 162 having a second diameter D2, and a third portion 164 having a third diameter D3. The device 102 further includes the inlet 106 located adjacent the first portion 160 wherein the inlet 106 is configured for receiving the biological sample 110. An outlet 108 is located adjacent the third portion 164 and the second portion 162 is located between the first portion 160 and third portion 164. The first D1, second D2, and third D3 diameters can progressively decrease in size in order to form a tapered, stepped, or conical structure which will improve the separation time of plasma. It can be appreciated that the stepped design is not limited to three different diameters but rather can have multiple diameters moving in a decreasing size from the inlet to the outlet of the container, approaching a conical shape.

The device further includes a separator 130 located within the container for separating the biological sample into the first phase 114 and the second phase 116. The particular structures shown in FIGS. 5, 6A, and 6B help in processing a large volume of biological fluid initially by reducing the overall resistance as well as avoiding clogging of the separator 130. It can be appreciated that the separator 130 can comprise one or more series of filters 132 having variable or decreasing pore sizes and/or multiple stages filled with different grades of filters 132. The device 102 further includes a member for creating a pressure gradient 140 across the separator 130 to increase a rate of movement of the biological sample 110 through the separator 130 such that the first phase 114 exits the separator 130 prior to the second phase 116. The pressure gradient 140 can include a first pressure P1 located at the inlet 106 of the container 104 and a second pressure P2 located at the outlet 108 of the container 104. The first pressure P1 is greater than the second pressure P2 to facilitate movement of the biological sample 110 through the separator 130. The member for creating the pressure gradient 140 can be one of several devices discussed in detail below.

With continuing reference to FIGS. 7A and 7B, the device can also include a narrow feed channel 170 having a diameter D4 which is less than the first diameter D1 of the first portion 160. By having a narrow feed channel 170 to introduce the biological sample 110 into the device 102, there is always a column of the sample in the channel and, thus, the chance of air entering the system, as shown by arrow 172 in FIG. 7A, is minimized. This allows the device 102 to be held at any angle avoiding any orientation dependence in the system.

Reference is now made to FIGS. 8 and 9 which show a device, generally indicated as 202 for separation of a biological sample 210 into a first phase 214 and a second phase 216. The device 202 includes a holder 205 including an inlet 206 and an outlet 208. The inlet 206 is configured for receiving the biological sample 210. The device 202 further includes a separator 230 in the form of at least one lateral flow strip 232 cooperating with the holder 205 for separating the biological sample 210 into the first phase 214 and the second phase 216. A member for creating a pressure gradient 240 across the lateral flow strip 232 is provided to increase a rate of movement of the biological sample 210 through in a lateral direction L through the lateral flow strip 232 such that the first phase 214 exits the flow strip 232 and the outlet 208 prior to the second phase 216. A single strip is limited by how much volume it can process in the lateral direction. Accordingly, in order to process larger volumes of samples, as shown in FIG. 9, the separator 230 can comprise a plurality of lateral flow strips 232 stacked one upon another. Additionally, the lateral flow strips 232 can have a trapezoidal shape having a large base 244 and a small base 246 wherein the large base 244 is positioned adjacent the inlet 206 of the holder 205, and the small base 246 is positioned adjacent the outlet of the holder 205.

Reference is now made to FIGS. 10A-10C which show different modes for the driving pressure gradients 40, 140, 204 for facilitating the separation of the biological samples 10, 110, 210 as discussed in the above arrangements. The pressure gradient can be constant, increasing, decreasing, or any combination thereof. The relevant pressure modes for a passive device would include a decreasing pressure for collection tubes 42, such as shown in FIG. 10A or an increasing pressure mode, for example when using a syringe 44, as shown in FIG. 10B. A third mode, as shown in FIG. 10C, could involve a pressure regulator 46 to generate a desired pressure profile for separating plasma or a first phase 14. This can be used in a core lab for separating plasma on the analyzer directly.

Figures 11, 11A, 11B, 11C, 11D:
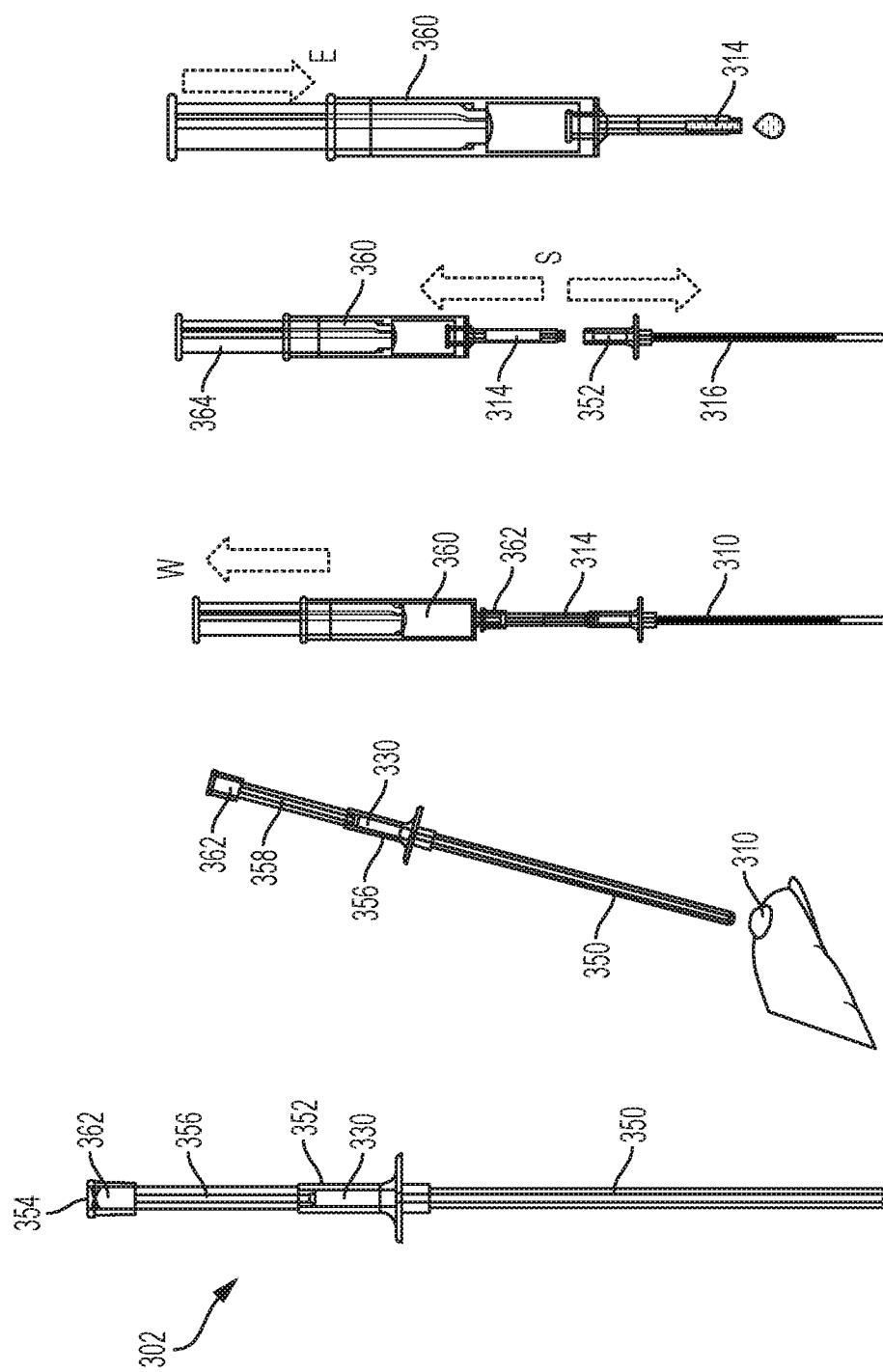
FIG. 11 is a side perspective view of a chromatographic depth filtration device for processing a capillary biological sample in accordance with an embodiment of the invention.
FIGS. 11A-11D are sequential side perspective views of the separation of the biological sample using the device of FIG. 11 in accordance with an embodiment of the invention.

Reference is now made to FIG. 11 which shows a device, generally indicated as 302, and FIGS. 11A-11D which show a sequential method for the collection and separation of a biological sample 310 into a first phase 314 and a second phase 316. The device 302 includes a capillary tube 350 configured for receiving the biological sample 310 via capillary pressure. A separation container 352 is associated with the capillary tube 350. The container 352 includes an outlet 354. A separator 330 is located within the separation container 352 for separating the biological sample 310 into the first phase 314 and the second phase 316. It can be appreciated that the separator 330 can comprise a plurality of filters or be formed of a fibrous filter material having any of the characteristics discussed in detail above. A member, such as a syringe 360, is associated with the container outlet 354 for creating a pressure gradient across the separator 330 to increase a rate of movement of the biological sample 310 through the separator 330 to facilitate separation of the first phase 314 from the second phase 316. The container 352 can further include a first phase collection chamber 356. According to one embodiment, a luer lock 362 can be provided at the outlet 354 of the container 352 adjacent the first phase collection chamber 356 for connecting the collection chamber 356 to the syringe 360. The first phase collection chamber 356 can be removably attached with the separation container 352 so that after separation of the sample 310 and collection of the first phase 314 into the collection chamber 356, the collection chamber 356 can be removed from the separation chamber 352.

As shown in FIGS. 11A-11D, during operation, a biological sample 310, such as blood, is received in the capillary tube 350. A syringe 360 is attached to the outlet 354 of the device 302. A plunger 364 is then pulled or withdrawn, as shown by arrow "W" to apply a drawing force on the sample 310 to pull the sample 310 through the separator 330 for separating the first phase 314 or plasma from the sample 310. Once the first phase 314 is drawn into the first phase collection chamber 356, the first phase collection chamber 356 is separated from the separation chamber 352, as shown by arrow S in FIG. 11C. The first phase 314 is now ready to be transferred to a diagnostic testing device. This transference can be accomplished by pressing the plunger 364, as shown by arrow E in FIG. 11D, to eject the first phase 314.

Reference is now made to FIG. 12 which shows a device, generally indicated as 402, and FIGS. 12A-12D which show a sequential method for the collection and separation of a biological sample 410 into a first phase 414 and a second phase 416. The device 402 includes a collection chamber 470 having an inlet 472 for collecting the biological sample 410 via venous pressure. A separation chamber 474 is associated with the collection chamber 470 and a separator 430 is located within the separation chamber 474 for separating the biological sample 410 into the first phase 414 and the second phase 416. A capillary tube 476 is associated with the separation chamber 474 wherein the capillary tube 476 includes a first end 477 configured for receiving the first phase 414. The capillary tube also includes a second end 478. A member, such as a syringe 460, can be associated with the second end 478 of the capillary tube 476 for creating a pressure gradient across the separator 430 to increase a rate of movement of the biological sample 410 through the separator 430 to facilitate separation of the first phase 414 from the second phase 416. The collection chamber 470 can include a luer lock 466 for connecting the collection chamber to a biological collection system or blood collection system well known in the art. The second end of the capillary tube 476 can include a luer lock 462 for connecting to the syringe 460.

It can be appreciated that the separator 430 can comprise a plurality or stack of filter elements and/or can include one or more filters formed of a fibrous material as discussed in detail above. Additionally, the capillary tube 476 is separable from the separation chamber 474 such that after separation of the sample 410 and collection of the first phase 414 into the capillary tube 476, the capillary tube 476 can be removed from the separation chamber 474.

As shown in FIGS. 12A-12D, during operation, the biological sample 410, such as blood, is drawn into the collection chamber 470 using a conventional blood collection system. A syringe 460 is attached to the outlet 478 of the capillary tube 476 via luer lock 462. The plunger 464 is then pulled or withdrawn, as shown by arrow W to apply a drawing force on the sample 410 to pull the sample 410 through the separator 430 for separating the first phase 414 or plasma from the sample 410. Once the first phase 414 is drawn into the capillary tube 476, the capillary tube 476 is separated from the separation chamber 474, as shown by arrow S in FIG. 12C. The first phase 414 is now ready to be transferred to a diagnostic testing device. This transference can be accomplished by pressing the plunger 464, as shown by arrow E in FIG. 12D, to eject the first phase 414.

Reference is now made to FIG. 13 which shows a device, generally indicated as 502, and FIGS. 13A-13D which show a sequential method for the collection and separation of a biological sample 510 into a first phase 514 and a second phase 516 using a venous biological sample, such as a venous blood sample with the separation device as part of the sample collection device to directly collect the first phase 514 or plasma directing into an evacuated tube. The device 502 includes a collection chamber 570 having an inlet 572 for collecting the biological sample 510 via venous pressure such as with the use of a conventional blood collection device. According to one embodiment, a luer lock 566 can be provided to connect the device 502 with the blood collection device. The device 502 includes a separation chamber 574 associated with the collection chamber 570. A separator 530 is located within the separation chamber 574 for separating the biological sample 510 into the first phase 514 and the second phase 516. A cannula 580 is provided having a first end 581 associated with the separation chamber 574. A holder 583 is provided and a second end 582 of the cannula extends therein. A vacuum tube 584 is positioned within the holder 583 and is associated with the separation chamber 574 via the second end 582 of the cannula 580. According to one embodiment, a self-sealing stopper 585 can be provided on the vacuum tube, which can be pierced by the second end 582 of the cannula 580. The vacuum tube 584 pulls a vacuum and applies a pressure gradient across the separator 530 to increase a rate of movement of the biological sample 510 through the separator 530 to facilitate separation of the first phase 514 from the second phase 516 and to cause the first phase 514 to enter into the vacuum tube 584 via the cannula 580.

As discussed in detail above, the separator 530 can comprise a plurality of filters of varying porosity and/or one or more filters formed of a fibrous material. The collection chamber 570 and the separation chamber 574 are separable from the vacuum tube 584 such that after separation of the sample 510 and collection of the first phase 514 into the vacuum tube 584, the collection chamber 570 and separation chamber 574 can be removed from the vacuum tube 584.

As shown in FIGS. 13A-13D, during operation, the biological sample 510, such as blood, is drawn into the collection chamber 570 using a conventional blood collection system. The vacuum tube 584 is inserted into holder 583 and stopper 585 is pierced by cannula 580. As shown in FIG. 13B, upon attachment of the vacuum tube 584, vacuum pressure is applied to the sample 510 through the cannula to pull the sample 510 through the separator 530 for separating the first phase 514 or plasma from the sample 510. The first phase 514 is then pulled directly into the vacuum tube 584 as shown in FIG. 13C. The vacuum tube 584, which includes the self-sealing stopper 585, may now be removed from the device 502 for diagnostic testing, as shown in FIG. 13D.

Reference is now made to FIG. 14 which shows a device, generally indicated as 602, and FIGS. 14A-14E which show a sequential method for the collection and separation of a biological sample 610 into a first phase 614 and a second phase 616 using a venous biological sample, such as a venous blood sample, with the separation device located within an evacuated tube 690. The device 602 includes sample collection chamber 670, a separation chamber 674 associated with the sample collection chamber 670, a separator 630 located within the separation chamber 674 for separating the biological sample 610 into the first phase 614 and the second phase 616. A first phase collection chamber 676 having a first end 677 is associated with the separation chamber 674.

With continuing reference to FIGS. 14 and 14A-14E, the vacuum tube 690 is associated with the first phase collection chamber 676. The vacuum tube 690 is configured for applying a pressure gradient across the separator 630 to increase a rate of movement of the biological sample 610 through the separator 630 to facilitate separation of the first phase 614 from the second phase 616 and to cause the first phase 614 to enter into the first phase collection chamber 676. The separator 630 can be a plurality of filters of varying porosity and/or varying grades of porous filters as discussed in detail above. As shown in FIG. 14, the vacuum tube 690 can enclose the entire collection device. The vacuum tube 690 is closed via a self-sealing stopper 691. The device 602 can then be associated with any known biological collection device to collect a biological sample. The device 602 can also include a vented closure, such as a removable vented tip cap 692, associated with a second end 678 of the first phase collection chamber 676. This vented tip cap 692 is configured for providing fluid communication between the vacuum tube 690 and the first phase collection chamber 676. The first phase collection chamber 676 can also include a flexible membrane 693, which functions to expel the first phase 614 out of the first phase collection chamber 676, as shown in FIGS. 14D-14E, upon removal of the tip cap R and an application of a squeezing "SQ" force thereto.

As shown in FIGS. 14A-14E, during operation, the biological sample 610, such as blood, is drawn through self-sealing stopper 691 into the collection chamber 670 located within vacuum tube 690. The vacuum within the tube 690 acts to apply a pressure gradient to the sample 610 to pull the first phase 614 through the separator 630 at a faster rate than the second phase 616. After separation, the vacuum tube 690 can be removed from the collection device as shown by "S" in FIG. 14C. The first phase 614 is now ready to be transferred to a diagnostic testing device. This transference can be accomplished by removal of the vented tip cap 692, as shown in FIG. 14D and the application of a squeezing force "SQ" to the flexible member 693, as shown in FIG. 14E to expel the first phase 614 therefrom.

Reference is now made to FIG. 15 which shows a device, generally indicated as 702, and FIGS. 15A-15D which show a sequential method for the collection and separation of a biological sample 710 into a first phase 714 and a second phase 716 using a venous biological sample, such as a venous blood sample, with the separation device located within an evacuated tube 790. The device 702 includes sample collection chamber 770, a separation chamber 774 associated with the sample collection chamber 770, a separator 730 located within the separation chamber 774 for separating the biological sample 710 into the first phase 714 and the second phase 716. A first phase collection chamber 776 having a first end 777 is associated with the separation chamber 774.

With continuing reference to FIGS. 15 and 15A-15D, the vacuum tube 790 is associated with at least the first phase collection chamber 776. The vacuum tube 790 is configured for applying a pressure gradient across the separator 730 to increase a rate of movement of the biological sample 710 through the separator 730 to facilitate separation of the first phase 714 from the second phase 716 and to cause the first phase 714 to enter into the first phase collection chamber 776. The separator 730 can be a plurality of filters of varying porosity and/or varying grades of porous filters as discussed in detail above. As shown in FIG. 15, the vacuum tube 790 can enclose the entire collection device. The vacuum tube 790 is closed via a self-sealing stopper 791. The device 702 can then be associated with any known biological collection device to collect a biological sample. The device 702 can also include a vented closure, such as a bulbous shaped, flexible member 794 including apertures 795 extending through a wall portion. This vented flexible member 794 is configured for providing fluid communication between the vacuum tube 790 and the first phase collection chamber 776. The bulbous flexible member 794 is secured or integrally formed with the first phase collection chamber 776. After separation of the first phase 714 into the first phase collection chamber 776, the vacuum tube 790 can be removed and the first phase collection chamber 776 can be separated from the collection and separation chambers 770 and 774, as shown in FIG. 15C. The bulbous flexible member 794 then functions to expel the first phase 714 out of the first phase collection chamber 776, as shown in FIG. 15D, upon the application of a squeezing SQ force thereto.

As shown in FIGS. 15A-15D, during operation, the biological sample 710, such as blood, is drawn through self-sealing stopper 791 into the collection chamber 770 located within vacuum tube 790. The vacuum within the tube 790 acts to apply a pressure gradient to the sample 710 to pull the first phase 714 through the separator 730 at a faster rate than the second phase 716. After separation, the vacuum tube 790 can be removed from the collection device and the first phase collection chamber 776 can be removed from the separation chamber 774 as shown by S in FIG. 15C. The first phase 714 is now ready to be transferred to a diagnostic testing device. This transference can be accomplished by the application of a squeezing force "SQ" to the flexible bulbous member 794, as shown in FIG. 15D, to expel the first phase 714 therefrom.

The proposed plasma separation technology of the present invention provides the following advantages over the techniques currently in use: (A) rapid flow through plasma separation for small and large blood volumes eliminating the need for centrifugation; (B) the presence of an additional filter at the end of the separation column can further restrict particle passage, screening out the smallest cellular material such as platelets or debris; (C) provides low cost designs for both passive and active plasma separation and dispensing; and (D) the 3-D configuration minimizes device size which can be incorporated into feasible product.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the claims appended and any and all equivalents thereof.

The invention claimed is:

1. A device for separation of a blood sample into a first phase and a second phase, said device comprising:
   a container including an inlet and an outlet, said inlet configured for receiving the blood sample and having a larger opening area than said outlet;
   separator located within said container for separating the blood sample into the first phase and the second phase, said separator comprising a first filter, a second filter, and at least a third filter, said first filter, said second filter, and said at least a third filter each having a different grade having decreasing pore sizes from the first filter to the at least a third filter to progressively filter out different components of the blood sample to yield the first phase, said first filter being an open cell foam positioned at the inlet and configured to separate the blood sample into the first phase and the second phase, said second filter extending directly from the open cell foam to said at least third filter, said second filter being a fibrous structure that slows particles located within the second phase to further slow the flow of the second phase and increase a flow of the first of the first phase through the separator, said at least a third filter being a cell capture filter disposed in the container, positioned at the outlet; and
   a member for creating a pressure gradient across the separator to increase a rate of movement of the blood sample through the separator such that the first phase exits the separator prior to the second phase, said member being connected to said container.

2. The device of claim 1, including a dry anticoagulant material disposed on at least one of said open cell foam, said fibrous structure, and said cell capture filter.

3. The device of claim 1, wherein the separator has been treated to include at least one of a hydrophobic, hydrophilic, or reactive internal pore surface.

4. The device of claim 1, wherein the pressure gradient comprises a first pressure located at the inlet of the container and a second pressure located at the outlet of the container and wherein the first pressure is greater than the second pressure.

5. The device of claim 1, wherein the member for creating the pressure gradient includes a pressure regulator for controlling the pressure gradient to generate a pressure profile and wherein the pressure gradient is one of an increasing or decreasing pressure.

6. A device for separation of a blood sample into a first phase and a second phase, said device comprising:
   a container including at least a first portion having a first diameter, a second portion having a second diameter, and a third portion having a third diameter;
   an inlet located proximate the first portion, said inlet configured for receiving the blood sample;
   an outlet located proximate the third portion wherein the second portion is located between the first and third portion, said inlet having a larger opening area than said outlet;
   a separator located within the container and disposed between the inlet and the outlet, the separator for separating the blood sample into the first phase and the second phase, wherein the separator comprises a first filter positioned at the inlet, a second filter located in the second portion, and at least a third filter positioned at the outlet, said first filter, said second filter, and said at least a third filter each having a different grade having decreasing pore sizes from the first filter to the at least a third filter to progressively filter out different components of the blood sample to yield the first phase, said second filter extending directly from said first filter to said at least a third filter; and
   a member for creating a pressure gradient across the separator to increase a rate of movement of the blood sample through the separator such that the first phase exits the separator and the outlet prior to the second phase, and wherein the first, second, and third diameters progressively decrease in size with the first diameter being the largest in size and the third diameter being the smallest in size, said member being connected to said container.

7. The device of claim 6, wherein the at least one of the first, second, and third portions has a conical or tapered structure.

8. The device of claim 6, wherein the inlet comprises a narrow feed channel having a diameter which is less than the first diameter of the first portion.

9. A device for the collection and separation of a blood sample into a first phase and a second phase, said device comprising:
 a capillary tube configured for receiving the blood sample, the capillary tube including an inlet to receive the blood sample and an outlet, said inlet having a larger opening area than said outlet;
 a container connected to the outlet of the capillary tube to receive the blood sample from the capillary tube, the container comprising a separation chamber and a removable first phase collection chamber connected thereto, the separation chamber having a first end and a second, opposite end,
 a separator located within the separation chamber for separating the blood sample into the first phase and the second phase, wherein the separator comprises a first filter positioned at the first end, a second filter, and at least a third filter positioned at the second end, wherein said first filter, said second filter, and said at least a third filter each have a different grade having decreasing pore sizes from the first filter to the at least a third filter to progressively filter out different components of the blood sample to yield the first phase, said second filter extending directly from said first filter to said at least a third filter; and
 a member connected to an outlet of the container for creating a pressure gradient across the separator to increase a rate of movement of the blood sample through the separator such that the first phase exits the separator prior to the second phase and into the first phase collection chamber,
 wherein after separation of the sample and collection of the first phase into the first phase collection chamber, the first phase collection chamber can be removed from the separation chamber.

10. The device of claim 9, wherein the separator comprises at least one filter formed of a fibrous material.

11. The device of claim 10, wherein the member for creating the pressure gradient comprises a syringe.

12. The device of claim 11, wherein the collection chamber includes a luer lock for connecting the collection chamber to the syringe and wherein the syringe is adapted to force the first phase out of the collection chamber.

13. A device for the collection of a blood sample and separation of the blood sample into a first phase and a second phase, said device comprising:
 a collection chamber having an inlet for collecting the blood sample via venous pressure;
 a separation chamber connected to the collection chamber, the separation chamber having a first end and a second, opposite end;
 a separator located within the separation chamber for separating the blood sample into the first phase and the second phase, wherein the separator comprises a first filter positioned at the first end of the separation chamber, a second filter, and at least a third filter positioned at the second end of the separation chamber, wherein said first filter, said second filter, and said at least a third filter each have a different grade having decreasing pore sizes from the first filter to the at least a third filter to progressively filter out different components of the blood sample to yield the first phase, said second filter extending directly from said first filter to said at least a third filter;
 a capillary tube connected to the separation chamber, the capillary tube having a first end and a second end opposite the first end of the capillary tube; and
 a member connected to the second end of the capillary tube for creating a pressure gradient across the separator to increase a rate of movement of the blood sample through the separator to facilitate separation of the first phase from the second phase,
 wherein the capillary tube is separable from the separation chamber and wherein after separation of the sample and collection of the first phase into the capillary tube, the capillary tube can be removed from the separation chamber.

14. The device of claim 13, wherein the separator comprises at least one filter formed of a fibrous material.

15. The device of claim 13, wherein the member for creating the pressure gradient comprises a syringe.

16. The device of claim 13, wherein the collection chamber includes a luer lock for connecting the collection chamber to a biological collection system and wherein the second end of the capillary tube includes a luer lock for connecting to a syringe.

* * * * *

UNITED STATES PATENT AND TRADEMARK OFFICE
CERTIFICATE OF CORRECTION

PATENT NO. : 10,578,606 B2
APPLICATION NO. : 15/252804
DATED : March 3, 2020
INVENTOR(S) : Kishore K. Bokka Srinivasa Rao et al.

It is certified that error appears in the above-identified patent and that said Letters Patent is hereby corrected as shown below:

In the Claims

Column 13, Line 63, Claim 1, before "separator" insert -- a --

Column 14, Lines 11-12, Claim 1, after "first" delete "of the first"

Signed and Sealed this
Nineteenth Day of May, 2020

Andrei Iancu
*Director of the United States Patent and Trademark Office*